(12) United States Patent
Kimura et al.

(10) Patent No.: US 9,114,970 B2
(45) Date of Patent: Aug. 25, 2015

(54) DISPENSING DEVICE AND NUCLEIC ACID ANALYZER

(75) Inventors: Ryusuke Kimura, Hitachinaka (JP); Yoshiyuki Shoji, Mito (JP); Shuhei Yamamoto, Mito (JP)

(73) Assignee: HITACHI HIGH-TECHNOLOGIES CORPORATION, Tokyo (JP)

( * ) Notice: Subject to any disclaimer, the term of this patent is extended or adjusted under 35 U.S.C. 154(b) by 65 days.

(21) Appl. No.: 13/811,940

(22) PCT Filed: Jul. 6, 2011

(86) PCT No.: PCT/JP2011/003847
§ 371 (c)(1),
(2), (4) Date: Jan. 24, 2013

(87) PCT Pub. No.: WO2012/014388
PCT Pub. Date: Feb. 2, 2012

(65) Prior Publication Data
US 2013/0121882 A1 May 16, 2013

(30) Foreign Application Priority Data
Jul. 29, 2010 (JP) ............................... P2010-169968

(51) Int. Cl.
*B67D 7/02* (2010.01)
*G01N 35/10* (2006.01)
*G01N 35/00* (2006.01)
*G01N 35/04* (2006.01)

(52) U.S. Cl.
CPC .......... *B67D 7/0288* (2013.01); *G01N 35/1002* (2013.01); *G01N 35/1081* (2013.01); *G01N 2035/00277* (2013.01); *G01N 2035/0405* (2013.01)

(58) Field of Classification Search
USPC .............. 422/82.08, 501, 512, 516, 517, 519, 422/521, 926, 927; 73/1.74, 1.05; 222/71, 222/173, 494; 436/51, 54; 141/250
See application file for complete search history.

(56) References Cited

U.S. PATENT DOCUMENTS

| | | |
|---|---|---|
| 5,039,615 A | 8/1991 | Takahata |
| 2005/0196778 A1* | 9/2005 | Yamamoto et al. ............... 435/6 |
| 2008/0063570 A1* | 3/2008 | Fujino et al. .................... 422/99 |

FOREIGN PATENT DOCUMENTS

| | | |
|---|---|---|
| JP | 59-000638 | 1/1984 |
| JP | 64-003565 | 1/1989 |
| JP | 64-53167 | 3/1989 |
| JP | 2005-181145 | 7/2005 |
| JP | 2005-189034 | 7/2005 |
| JP | 2005-324832 | 11/2005 |
| JP | 2009-180605 | 8/2009 |

* cited by examiner

*Primary Examiner* — Jill Warden
*Assistant Examiner* — Julie Tavares
(74) *Attorney, Agent, or Firm* — Baker Botts L.L.P.

(57) ABSTRACT

A dispensing device that achieves both of preventing cross-contamination between reagents and attaching a lid to a reagent container is provided.

The dispensing device of the present invention includes a dispensing nozzle 10 that aspirates and discharges liquid, a lid opening and closing part 26 that projects downward to be lower than the dispensing nozzle 10, and a drive unit that makes the dispensing nozzle 10 and the lid opening and closing part 26 drive in the vertical direction, in which the dispensing nozzle 10 drives in the vertical direction independently of the lid opening and closing part 26. The dispensing device that achieves both of preventing cross-contamination between the reagents and attaching the lid to the reagent container can be provided.

6 Claims, 8 Drawing Sheets

DISPENSING DEVICE AND NUCLEIC ACID ANALYZER

TECHNICAL FIELD

The present invention relates to a dispensing device and a nucleic acid analyzer.

BACKGROUND ART

In order to automatically transfer various liquid such as a reagent, sample, specimen and the like set to an apparatus to an optional position, a dispensing robot is commonly used. The dispensing robot is a unit that makes the inside of a specific range of the apparatus drive two-dimensionally or three-dimensionally, and automatically executes aspiration and discharge of the liquid by a nozzle, tip and the like (hereinafter referred to as "nozzle") attached at the distal end thereof. The dispensing robot is used in various apparatuses such as various automatic analyzers and the like.

In various automatic analyzers and the like, liquid to be transferred (hereinafter referred to as "reagent") is expensive in many cases. Therefore, it is necessary to minimize the use amount of a reagent required for analysis. Also, in a case of medical equipment, when transfer of liquid fails due to some cause, it is necessary to display an error so as not to lead to an erroneous diagnosis. Accordingly, a method is commonly employed in which the liquid level is detected, an amount of attachment of a nozzle to a reagent is reduced, and the use amount of the reagent is minimized. With respect to detection of the liquid level, a capacitance method in which the nozzle is made an electrode is commonly employed. By employing this method, even when the number of the container containing the reagent increases, the liquid level can be detected for all containers by one liquid level detecting function. In detecting the liquid level by the capacitance method, because the nozzle is made an electrode, it is necessary to avoid that the nozzle contacts components other than the reagent. The reason is that, when the nozzle contacts a component other than the reagent, the component contacted may be erroneously detected as the liquid level.

On the other hand, in various automatic analyzers and the like, a reagent may occasionally be required to be set to an apparatus for a long time. When the reagent is set to the apparatus for a long time, evaporation of the reagent, deterioration of the chemical components and the like are inevitable. However, the more the use amount of the reagent is reduced, the more the effect of evaporation of the reagent and deterioration of the chemical components increases. Thus, reliability of the analysis result may be damaged. In order to prevent evaporation of the reagent and deterioration of the chemical components, the air must be blocked in addition to a method of cooling the reagent.

In order to achieve both of the two functions, the reagent must be blocked against the air as much as possible while the nozzle does not contact other than the reagent. Required degree of blockage and method of blocking against the air differ according to the apparatus because the composition and property of the reagent used and the use environment are different. In some cases, it is necessary to attach a lid to a reagent container to block the air more. When the lid is attached, because the nozzle and the lid contact with each other, erroneous detection may occur in the liquid level detection by the capacitance method. Therefore, a mechanism for opening and closing the lid is required separately. Since it is also forced to add a new drive mechanism for opening and closing the lid, defects such as significant increase of the cost, enlargement of the apparatus size, and increase of the noise generated are thereby developed.

As an improvement plan therefor, there is a method in which the lid is made of an electro-conductive elastic body, and the liquid level is detected after the nozzle penetrates the lid. However, in aspirating the reagent, the reagent attached to the nozzle is attached to the lid also. In aspirating the reagent again, the reagent having been attached to the lid before is attached up to the root of the nozzle. Thus, increase of cross-contamination between the reagents (separate reagents are mixed to each other) is worried about. In order to solve the problem, it is necessary to clean the nozzle from the root in cleaning the nozzle.

In cleaning the nozzle, pure water is commonly used. When the quantity of the pure water used increases, the capacity of the pure water set to the apparatus increases; the capacity of a container for storing a waste liquid also increases by that rate, and the apparatus size increases. Also, there is a defect that, because cleaning is executed from the root, the volume of the pure water attached to the nozzle increases, and the reagent is diluted by the pure water attached to the nozzle in aspirating the reagent.

CITATION LIST

Patent Literature

Patent Literature 1: Japanese Unexamined Patent Application Publication No. Heil-53167
Patent Literature 2: Japanese Unexamined Patent Application Publication No. 2005-324832

SUMMARY OF INVENTION

Technical Problem

The problem to be solved is to provide a dispensing device and a nucleic acid analyzer that achieve both of preventing cross-contamination between reagents and attaching a lid to a reagent container.

Solution to Problem

A dispensing device of the present invention includes a dispensing nozzle that aspirates and discharges liquid, a projection that projects downward to be lower than the dispensing nozzle, and a drive unit that makes the dispensing nozzle and the projection drive in the vertical direction, in which the dispensing nozzle drives in the vertical direction independently of the projection.

Advantageous Effects of Invention

A dispensing device and a nucleic acid analyzer that achieve both of preventing cross-contamination between reagents and attaching a lid to a reagent container can be provided.

DESCRIPTION OF EMBODIMENTS

Figure 4:
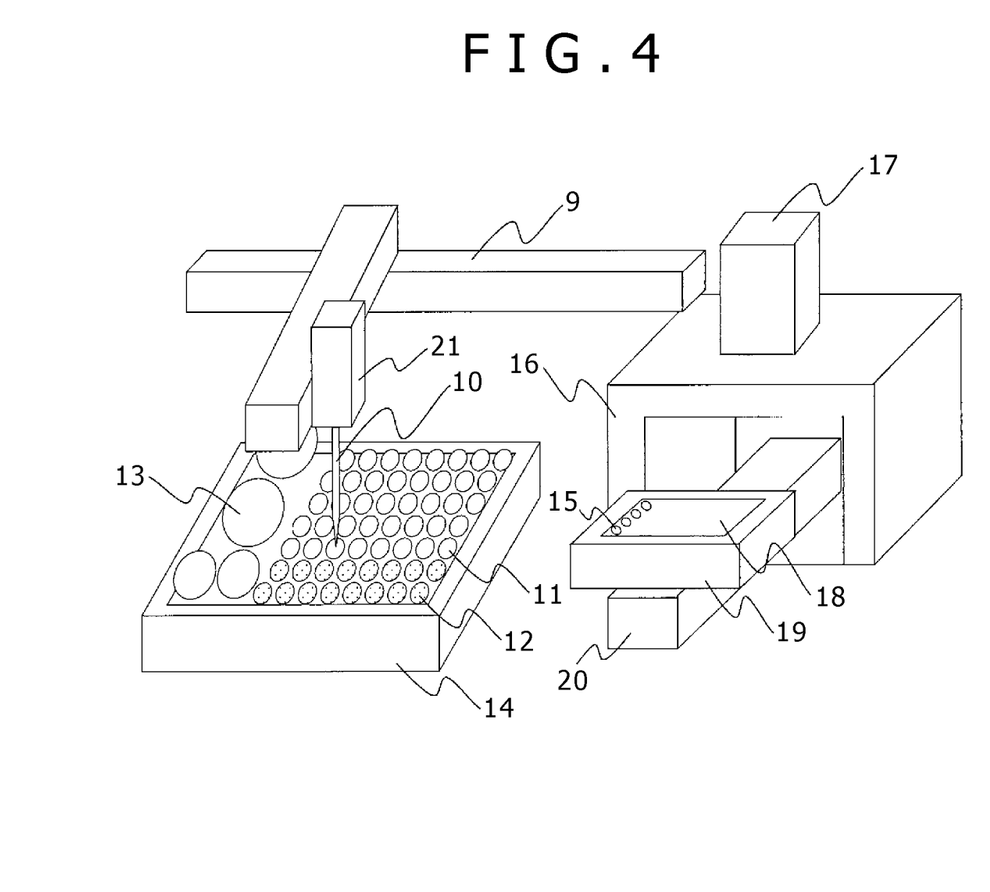
FIG. 4 is drawing showing a schematic constitution of a nucleic acid analyzer of the present invention.

FIG. 4 is an outline of a nucleic acid analyzer of the present invention. Reagents inside respective reagent containers 11, 13 arranged in a temperature controlled reagent rack 14 are sucked by a dispensing robot 9, and are injected from a reagent inlet 15 to a specimen sample plate 18. The dispensing robot (dispensing mechanism) 9 includes a Z-axis drive unit 21 and a dispensing nozzle 10.

A part of the reagent is injected after several kinds are mixed in a reagent mixing container 12. The specimen sample plate 18 is fixed to and temperature-controlled by a temperature control holder 19 and promotes a chemical reaction.

Thereafter, the specimen sample plate 18 fixed to the temperature control holder 19 is transported into an optical base 16 by a transporting stage 20.

By irradiating light emitted by a light source (not shown) inside a CCD camera unit 17 to the specimen sample plate 18 that has been transported into the optical base 16, fluorescence is emitted from the specimen sample plate 18, and the fluorescence is photographed by a CCD camera (not shown) inside the CCD camera unit 17. Nucleic acid is analyzed based on images photographed.

The present invention achieved both of liquid level detection by a capacitance method and prevention of evaporation of a reagent and deterioration of chemical components without arranging a new drive unit and software. Description will be given below in concrete terms.

First Embodiment

Figure 1:
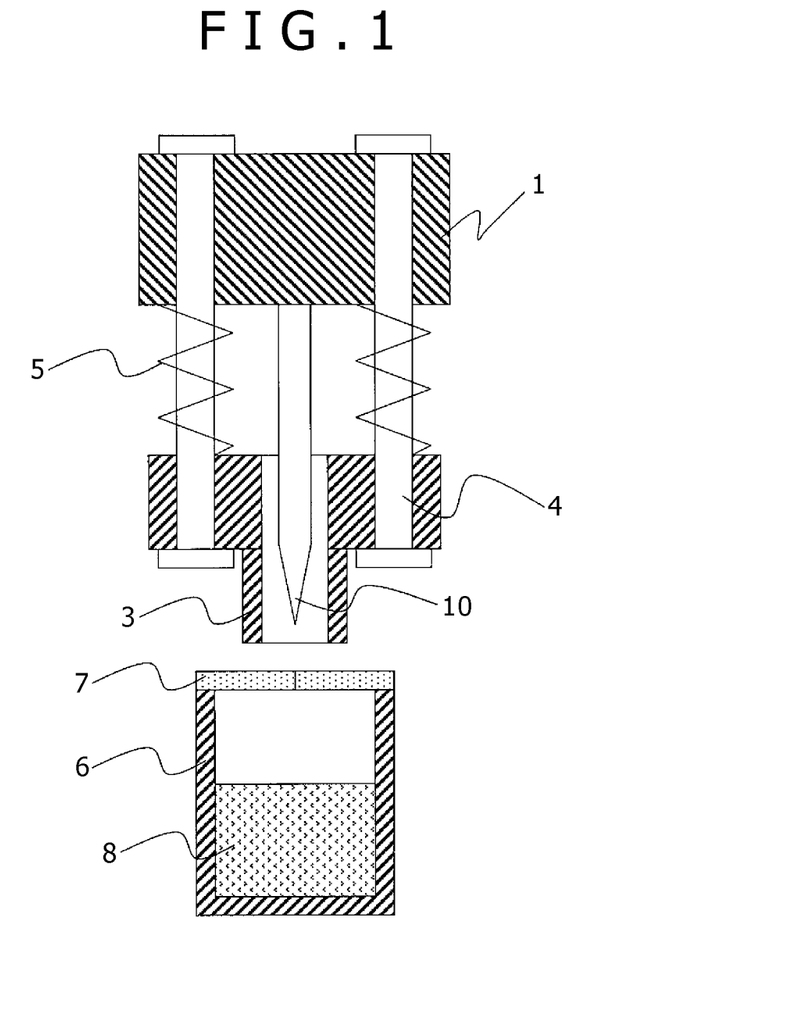
FIG. 1 is a schematic view showing a constitution of a part of a dispensing device of the present invention.

FIG. 1 is a schematic view showing a dispensing mechanism and a reagent container of the present invention.

The dispensing mechanism includes the dispensing nozzle 10 fixed to a Z-drive base 1, shafts 4 arranged around the dispensing nozzle 10 and penetrating the inside of the Z-drive base 1 in a drivable manner, and a lid opening and closing part 3 arranged at the distal ends of the shafts 4.

Between the Z-drive base 1 and the lid opening and closing part 3, springs 5 are arranged along the shafts 4. Also, the distal end of the lid opening and closing member 3 projects downward to be lower than the distal end of the dispensing nozzle 10. Further, the lid opening and closing member 3 is of a circular cylindrical shape whose inside is hollow, and the dispensing nozzle 10 is positioned in the hollow section. The shafts 4 connect the Z-axis drive base 1 and the lid opening and closing member 3 with each other, and the Z-axis drive base 1 can drive in the Z-axis direction along the shafts 4.

Also, in a reagent container 6, a lid 7 of a super elastic body with a notch is arranged.

Next, dispensing actions of the dispensing mechanism will be described.

Figure 2:
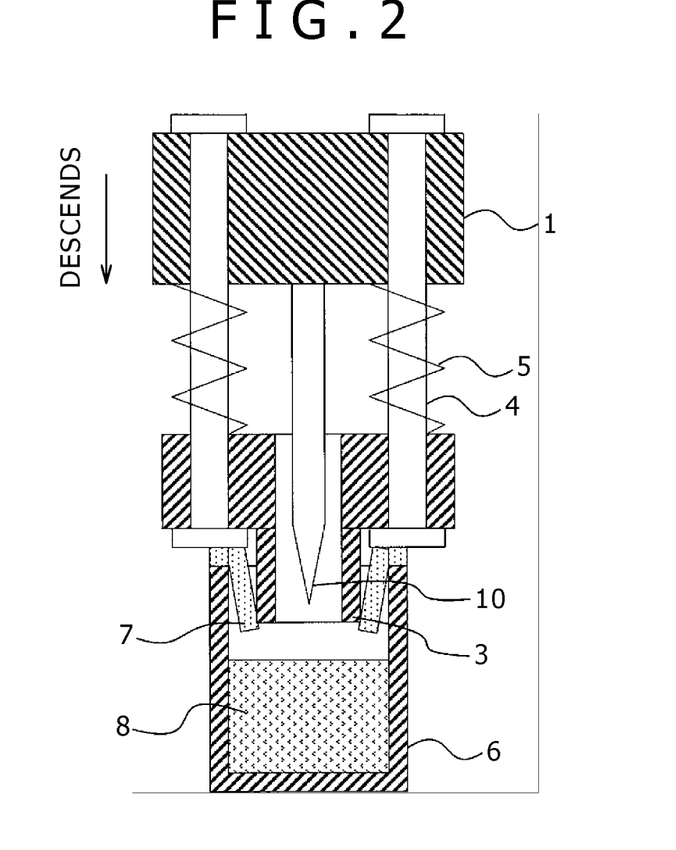
FIG. 2 is a schematic view showing a constitution of a part of a dispensing device of the present invention.
Figure 3:
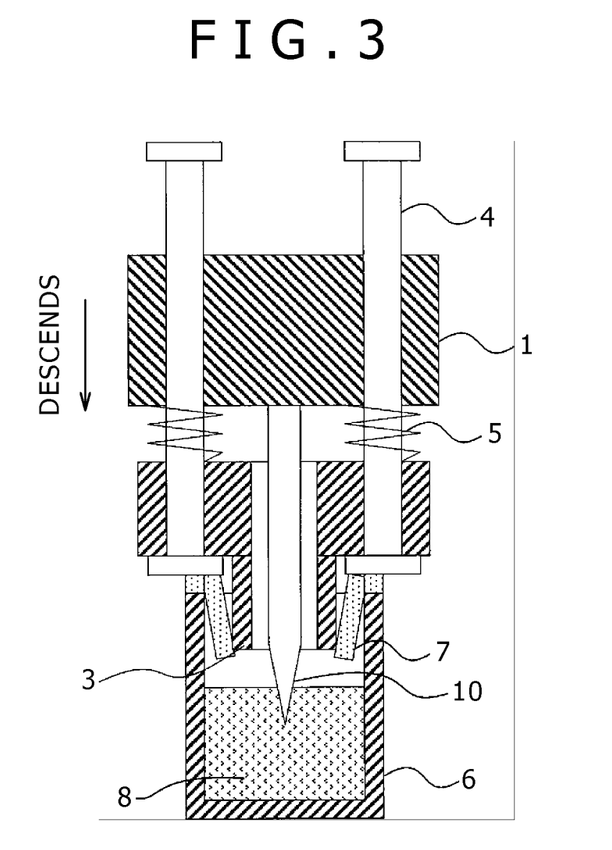
FIG. 3 is a schematic view showing a constitution of a part of a dispensing device of the present invention.

First, the dispensing mechanism moves downward toward the reagent container. As shown in FIG. 2, the lid opening and closing member 3 advances into the reagent container while pushingly opening the lid 7 of the reagent container 6. When the Z-drive base 1 further descends, because the springs 5 fixing the lid opening and closing part 3 sag, the Z-drive base 1 stops at a position where the lid 7 is pushingly opened. Thus, as shown in FIG. 3, the dispensing nozzle 10 can suck a reagent 8 without contacting the lid 7. When the dispensing nozzle 10 rises after aspirating the reagent 8, the lid 7 returns to an original position by elasticity of the lid 7 itself, and blocks the reagent 8 and the air against each other. Also, the lid opening and closing part 3 returns to the original position by own weight and friction with the lid 7.

Second Embodiment

Figure 5:
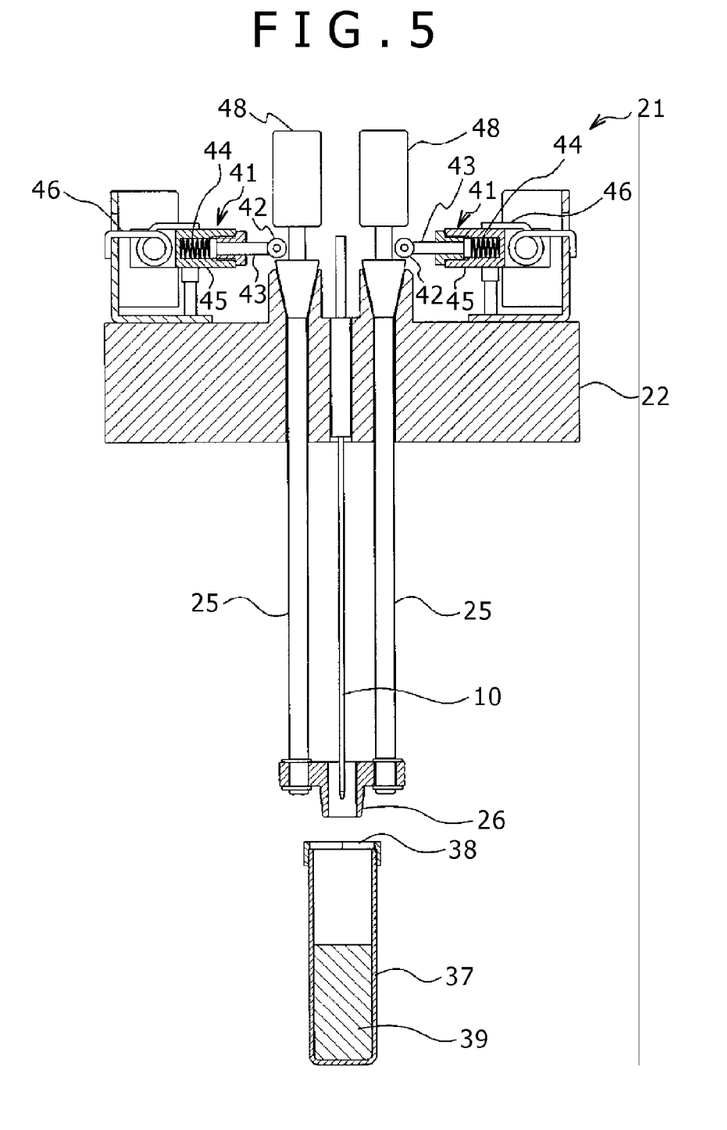
FIG. 5 is a schematic view showing a constitution of a part of a dispensing device of the present invention.

FIG. 5 is an embodiment different from that of FIG. 1 showing the detail of the Z-axis drive unit 21 of the dispensing robot (dispensing mechanism) 9.

The Z-axis drive unit will be described. The Z-axis drive unit includes a Z-axis drive base 22, two shafts 25 penetrate inside the Z-axis drive base 22, and shaft fixing members 41 are arranged at both sides of the shafts 25. The shaft fixing member 41 includes a shaft pressing member 43 including a rotating part 42 at the distal end, a spring 44 pressing the shaft pressing member 43 in the horizontal direction against the shaft 25, a case 45 holding the shaft pressing member 43 and the spring 44, and a torsion spring 46 pressing the case 45 downward. The torsion spring 46 is fixed to the Z-axis drive base 22.

Next, the shape of the upper side of the shaft 25 will be described. The upper side of the shaft includes a position where the diameter gradually increases as it goes upward and returns thereafter to the original dimension of the diameter, and is provided with a weight 48 further beyond thereof. As shown in FIG. 5, the shaft pressing member 43 presses the upper end of the position where the diameter increases most from above. The weight 48 presses the shaft 25 downward from above.

Also, similarly to the first embodiment, a lid opening and closing member 26 is arranged at the lower end of the shafts 25, and the dispensing nozzle 10 is arranged between the shafts 25. Further, the point that a notch is provided in a lid 38 of a reagent container 37 is similar to the first embodiment.

Next actions will be described using FIG. 5-FIG. 8.

Figure 6:
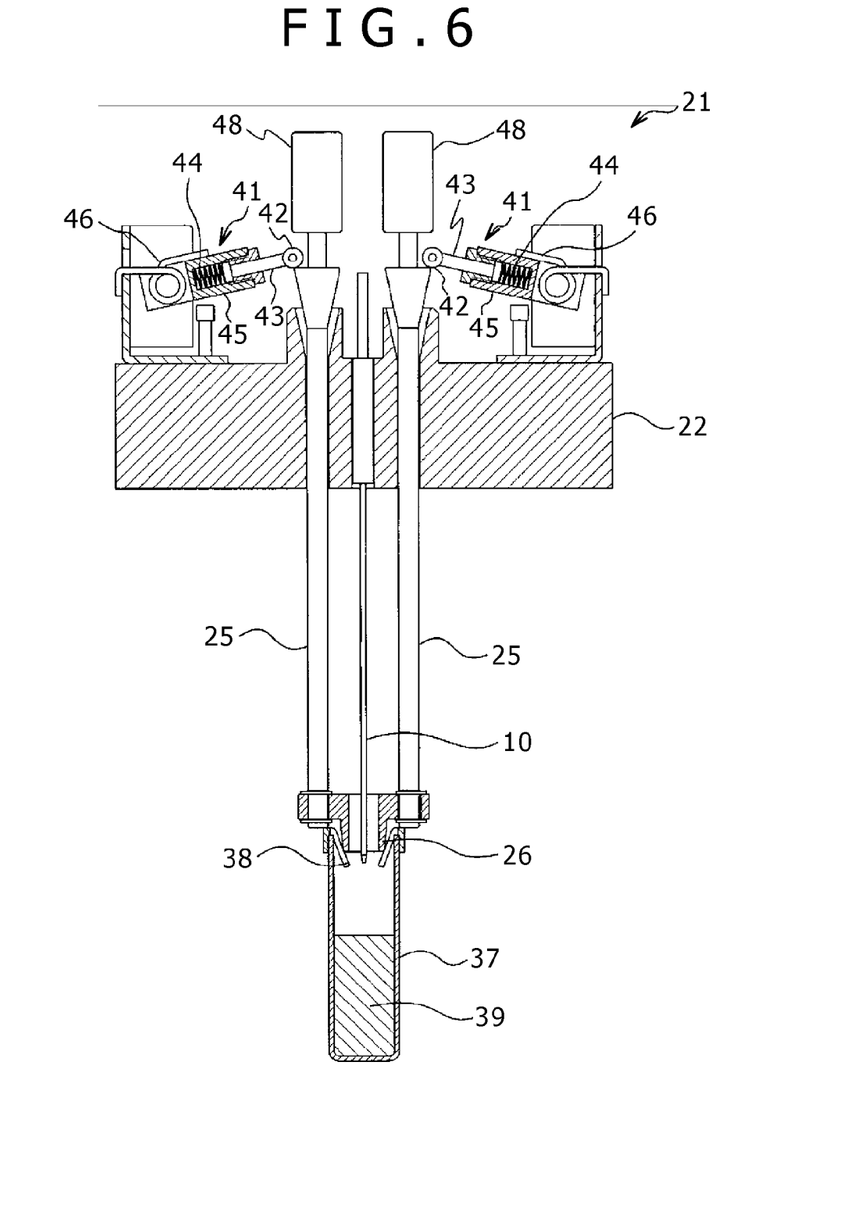
FIG. 6 is a schematic view showing a constitution of a part of a dispensing device of the present invention.

When the Z-axis drive base 22 descends from the initial position of FIG. 5, the lid opening and closing part 26 contacts the lid 38 first. The lid opening and closing part 26 is fixed to the shafts 25, the shafts 25 are applied with a load by the torsion springs 46, and therefore the lid 38 is pushingly opened by the load (FIG. 6).

Figure 7:
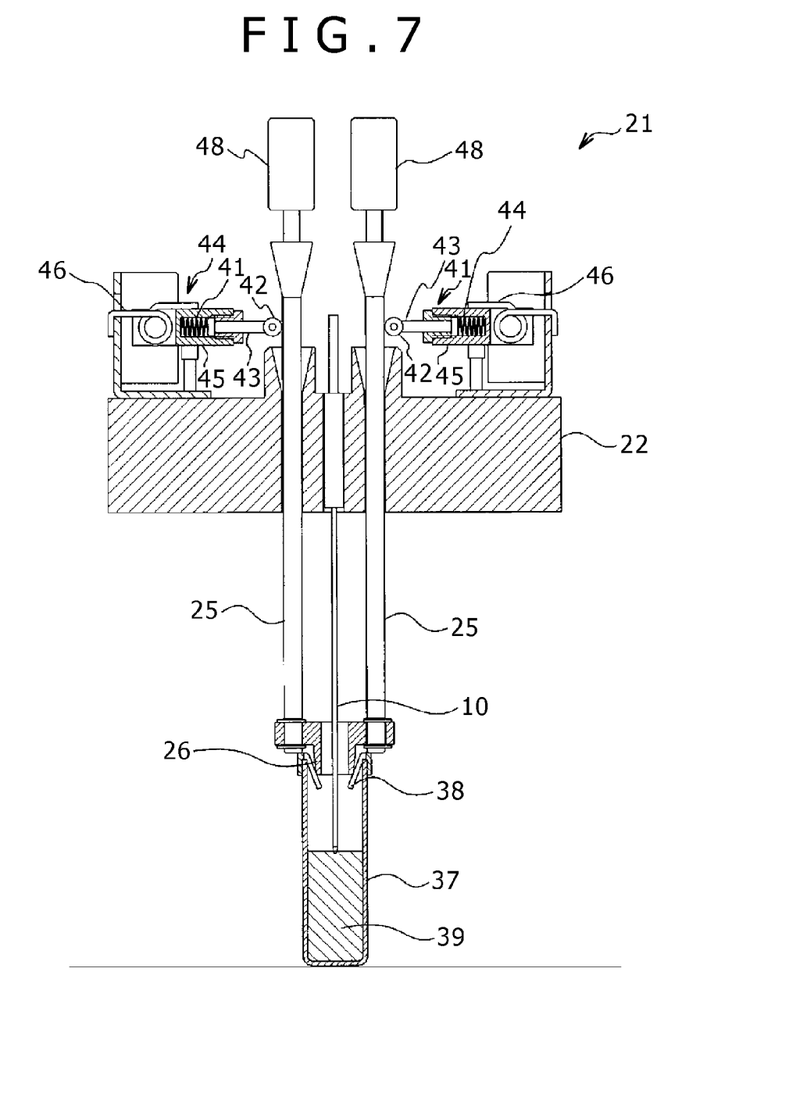
FIG. 7 is a schematic view showing a constitution of a part of a dispensing device of the present invention.

When the Z-axis drive base 22 descends further, the lid opening and closing part 26 contacts the edge of the reagent container 37 and stops, therefore the torsion springs 46 sag, and only the dispensing nozzle 10 descends (FIG. 7).

When the deflection amount of the torsion springs 46 exceed a constant amount, the shaft fixing members 41 override the position where the diameter of the shaft 25 increases and depart from the shafts 25, and the load to the shafts 25 is released.

Figure 8:
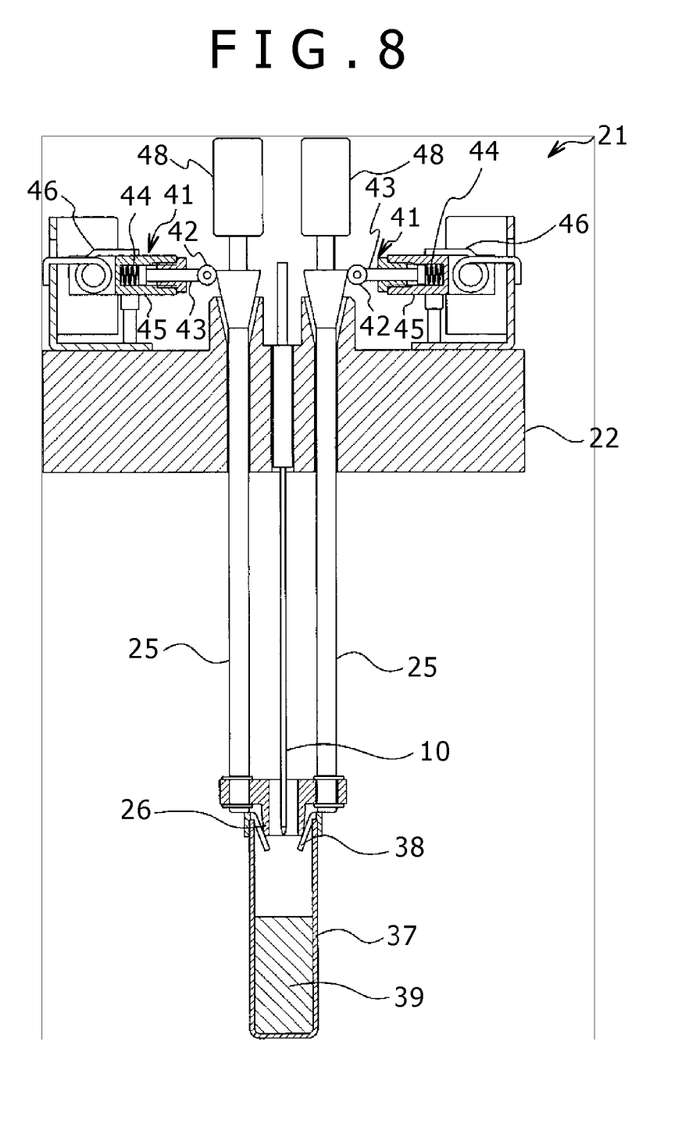
FIG. 8 is a schematic view showing a constitution of a part of a dispensing device of the present invention.

The dispensing nozzle 27 has a liquid level detecting function by the capacitance method, descends by a constant amount after detecting the liquid level of a reagent 39, and aspirates the reagent 39. After the reagent 39 is sucked, the Z-axis drive base 22 rises (FIG. 8). As the Z-axis drive base 22 rises, the lid opening and closing part 26 departs from the edge of the reagent container 37, and returns to the original position by own weight of the weights 48 and friction with the lid 38 (FIG. 5). The lid 38 also returns to the original position by own elasticity and friction with the lid opening and closing part 26.

By adopting the present configuration, the reagent 39 inside the reagent container 37 and the air can be blocked against each other at a time other than during aspirating while the dispensing nozzle 10 and the lid 38 of the reagent container 37 are not made contact with each other when the reagent 39 is sucked. Thus, both of liquid level detection by the capacitance method and prevention of evaporation and deterioration of the chemical components of the reagent 39 can be achieved, and reliability of aspirating the reagent and reliability of the analysis result improve.

Also, because the reagent 39 is not attached to the root of the dispensing nozzle 10 through the lid 38, contamination can be prevented, cleaning work of the dispensing nozzle 27 can be simplified, the cleaning time can be shortened, and the cleaning liquid quantity can be reduced. Also, because the torsion springs 46 for applying the load are disposed in the upper part of the Z-axis drive base 22, attachment of the reagent to the torsion spring 46 for some reason is prevented.

The torsion spring 46 for applying the load may be either a compression spring or an extension spring. However, when the compression spring and the extension spring are employed, if the bottom of the reagent container 37 is deep, in aspirating the reagent 39 from the reagent container 37, the deflection amount of the spring increases, and the load applied to the Z-axis drive base 22 increases.

By adopting the present structure that employs the torsion springs 46, because the load applied to the shafts is eliminated when the deflection amount exceeds a constant amount, the reagent container 37 with deep bottom can be also dealt with. In the present invention, the lid 38 that entirely opened once never closes even when the load applied to the shafts 25 is eliminated. However, when the bottom of the reagent container 37 is shallow, the structure can be simplified when the compression spring and the extension spring are used. Also, if it is possible to enlarge the weights 48 to secure the weight sufficient to be able to open the lid 38, the lid 38 may be opened and closed only by own weight of the weights 48.

By applying the present structure, actions other than opening and closing the lid 38 also become possible. If the lid 38 is not opened and closed and is to be penetrated to suck the reagent 39, in raising the nozzle 27 after aspirating the reagent, the reagent container 37 may also be lifted up together. On the other hand, by making the torsion spring 46 of the present structure a compression spring, extension spring and the like and applying a load to the reagent container 37 at all time, floating of the reagent container 37 can be prevented.

Also, by attaching a detection plate to the shafts 25 and the weights 48 of the present structure and recognizing the detection plate by a sensor, presence/absence of the reagent container 37 can be distinguished, and forgetting setting the reagent by a customer can be prevented.

When these functions are to be provided on the temperature controlled reagent rack 14 side, the sensors and the mechanisms are required by the number of the reagent containers. However, by providing these functions on the dispensing unit 9 side by the present invention, even if the number of the reagent containers increases, one sensor and one mechanism can deal with it.

Respective apparatuses including a dispensing robot, in which a lid must be attached to a reagent container in order to prevent evaporation of the reagent and deterioration of the chemical components. Also, respective apparatuses including a dispensing robot, in which the lid and the nozzle must be made not contact with each other in order to detect the liquid level by the capacitance method, to prevent contamination and to simplify a cleaning work, and due to other reasons. These apparatuses are achieved utilizing intrinsic movement of the dispensing robot then without arranging new drive mechanism and software and without limiting the intrinsic movement of the dispensing robot.

Respective apparatuses including a dispensing robot, in which the reagent container may possibly float up in aspirating the reagent, which is required to be prevented. A function for preventing floating up is mounted on the dispensing robot.

Respective apparatuses including a dispensing robot in which presence/absence of the reagent container is required to be detected, a function for detecting presence/absence of the reagent container is mounted on the dispensing robot.

By making the lid of the reagent container and the nozzle not contact with each other by the present invention, the liquid level can be detected by the capacitance method and evaporation and deterioration of the chemical components of the reagent can be prevented. Thus, reliability of aspirating the reagent and reliability of the analysis result improve. Also, because the nozzle and the lid are made not contact with each other, the reagent can be prevented from attaching to the nozzle through the lid. Thus, contamination can be prevented, nozzle cleaning can be simplified, the cleaning time can be shortened, and the system water required for nozzle cleaning can be reduced.

According to the structure of the present invention, because the lid of the reagent can be opened and closed without adding a new drive mechanism, the cost can be reduced, the space can be secured, and the noise generated can be reduced. Also, because the lid is opened and closed using only vertical movement the dispensing robot has, intrinsic movement of the dispensing robot is not limited. Further, because the lid opening/closing mechanism is mounted on the dispensing robot, even when the number of the reagent container increases, only one lid opening and closing part is required, and increase of the kind of the reagent can be dealt with easily.

LIST OF REFERENCE SIGNS

1 . . . Z-axis drive base
3, 26 . . . lid opening and closing part
4, 25 . . . shaft
5, 44 . . . spring
6, 11, 13 . . . reagent container
7 . . . lid
8 . . . reagent
9 . . . dispensing robot
10 . . . dispensing nozzle
12 . . . reagent mixing container
14 . . . temperature controlling reagent rack
15 . . . reagent inlet
16 . . . optical base
17 . . . CCD camera unit
18 . . . specimen sample plate
19 . . . temperature controlling holder
20 . . . transporting stage
21 . . . Z-axis drive unit
22 . . . Z-axis drive base
41 . . . shaft fixing member
42 . . . rotating part
43 . . . shaft pressing member
45 . . . case
46 . . . torsion spring
48 . . . weight

The invention claimed is:
1. A dispensing device, comprising:
a dispensing nozzle having a distal end and configured to aspirate and discharge liquid;
a lid opening and closing member comprising a projection that projects downward, the projection having a first position lower than the distal end of the dispensing nozzle and a second position above the distal end of the dispensing nozzle; and
a drive unit configured to drive the dispensing nozzle and the lid opening and closing member in the vertical direction, the dispensing nozzle being driven independently of the projection, the drive unit comprising:
a drive base joined to the dispensing nozzle and configured to drive in the vertical direction, the drive base having a first side and second side opposite the first side;
at least two shafts penetrating the drive base, the at least two shafts comprising:
a first end on the first side of the drive base,
a second end joined to the lid opening and closing member and positioned below the second side of the drive base, and
a portion near the first end having an increasing width towards the first end of the at least two shafts; and
a shaft fixing member comprising:
a case,
a shaft pressing member held by the case and having a distal end relative the case, the pressing member having a rotating part at the distal end, the rotating part having a first position above the portion of the at least two shafts having an increasing width and a second position departed from the at least two shafts,
a first spring held by the case, the first spring configured to press the shaft pressing member in a horizontal direction against the at least two shafts, and
a second spring joined to the drive base and configured to press the case downward.

2. The dispensing device according to claim 1, wherein the projection of the lid opening and closing member is a circular cylindrical member whose inside is hollow, and the distal end of the dispensing nozzle is stored in the hollow section.

3. The dispensing device according to claim 1, wherein the projection of the lid opening and closing member is configured to pushingly open a lid of a reagent container.

4. The dispensing device according to claim 1, wherein the second spring of the shaft fixing member is a torsion spring.

5. The dispensing device according to claim 1, wherein a weight is provided on the first end side of the at least two shafts.

6. The dispensing device according to claim 1, wherein a liquid level detecting function is provided at the distal end of the dispensing nozzle.

* * * * *